(12) United States Patent
Yang et al.

(10) Patent No.: US 7,604,967 B2
(45) Date of Patent: Oct. 20, 2009

(54) LIGNIN-BLOCKING TREATMENT OF BIOMASS AND USES THEREOF

(75) Inventors: Bin Yang, Hanover, NH (US); Charles E. Wyman, Norwich, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 422 days.

(21) Appl. No.: 10/391,740

(22) Filed: Mar. 19, 2003

(65) Prior Publication Data

US 2004/0185542 A1     Sep. 23, 2004

(51) Int. Cl.
*C12P 7/06* (2006.01)
(52) U.S. Cl. .................... 435/161; 530/378; 435/68.1; 435/99
(58) Field of Classification Search ............ 435/99, 435/165
See application file for complete search history.

(56) References Cited

U.S. PATENT DOCUMENTS

| | | | |
|---|---|---|---|
| 4,009,075 A * | 2/1977 | Hoge | 435/162 |
| 4,237,226 A | 12/1980 | Grethlein | |
| 4,556,430 A | 12/1985 | Converse et al. | |
| 4,668,340 A | 5/1987 | Sherman | |
| 4,708,746 A | 11/1987 | Hinger | |
| 4,746,401 A | 5/1988 | Roberts et al. | |
| 4,861,721 A | 8/1989 | Waterbury et al. | |
| 5,125,977 A | 6/1992 | Grohmann et al. | |
| 5,258,293 A | 11/1993 | Lynd et al. | |
| 5,424,417 A | 6/1995 | Torget et al. | |
| 5,503,996 A | 4/1996 | Torget et al. | |
| 5,529,663 A | 6/1996 | Springer | |
| 5,536,325 A | 7/1996 | Brink | |
| 5,688,674 A * | 11/1997 | Choi et al. | 435/162 |
| 5,705,369 A | 1/1998 | Torget et al. | |
| 5,837,506 A | 11/1998 | Lynd et al. | |
| 6,022,419 A | 2/2000 | Torget et al. | |
| 6,063,204 A | 5/2000 | Hester et al. | |
| 6,159,510 A | 12/2000 | Lizak | |
| 7,018,213 B2 * | 3/2006 | Marcus et al. | 434/322 |

FOREIGN PATENT DOCUMENTS

| | | |
|---|---|---|
| EP | 0 268 575 A2 * | 5/1988 |
| GB | 24738 A | 10/1914 |
| WO | WO 94/29474 | 12/1994 |

OTHER PUBLICATIONS

Minami et al. Characterization of clarified medium from submerse and semisolid cultivation of OF Aspergillus awamori NRRL3112 by size-exclusion chromatography. Braz. J. Chem. Eng. vol. 16 No. 2 Jun. 1999. pp. 1-7.*

Wyman, Charles E., "Biomass Ethanol: Technical Progress, Opportunities, and Commercial Challenges", Annu. Rev. Energy Environ. 1999, V. 24, pp. 189-226.

Wyman, Charles E., Spindler, Diane D., and Grohmann, Karel, "Simultaneous Saccharification and Fermentation of Several Lignocellulosic Feedstocks to Fuel Ethanol", Biomass and Bioenergy, 1992, vol. 3, No. 5, pp. 301-307, Pergamon Press Ltd., Great Britian.

Wyman, Charles E., "Ethanol from Lignocellulosic Biomass: Technology, Economics, and Opportunities", Bioresource Technology 50, 1994, pp. 3-16, Elsevier Science Limited, Great Britain.

Wyman, C.E., Spindler, D.D., Grohmann, K. and Lastick S.M., "Simultaneous Saccharification and Fermentation of Cellulose with the Yeast *Brettanomyces clausenii*", Biotechnology and Bioengineering Symp. No. 17, 1986, pp. 221-238.

Wyman, Charles E., "Twenty Years of Trials, Tribulations, and Research Progress in Bioethanol Technology", Applied Biochemistry and Biotechnology, 2001, V. 91-93, pp. 5-21, The Humana Press Inc.

Wright, John D., Wyman, Charles E. and Grohmann, Karel, "Simultaneous Saccharification and Fermentation of Lignocellulose", 1988, pp. 75-90, The Humana Press Inc.

Spindler, Diane D., Wyman, Charles E., Mohagheghi, Ali, and Grohmann, Karel, "Thermotolerant Yeast for Simultaneous Saccharification and Fermentation of Cellulose to Ethanol", 1988, pp. 279-293, The Humana Press Inc.

Spindler, Diane D., Wyman, Charles E., Grohmann, Karel and Philippidis, George P., "Evaluation of the Cellobiose-Fermenting Yeast *Brettanomyces custersii* in the Simultaneous Saccharification and Fermentation of Cellulose", Biotechnology Letters, May 1992, V. 14 No. 5, pp. 403-407.

Spindler, Diane D., Wyman, Charles E., and Grohmann, Karel, "The Simultaneous Saccharification and Fermentation of Pretreated Woody Crops to Ethanol", Applied Biochemistry and Biotechnology, 1991, vol. 28/29, pp. 773-786.

Spindler, Diane D., Wyman, Charles E., Grohmann, Karel and Mohagheghi, Ali, "Simultaneous Saccharification and Fermentation of Pretreated Wheat Straw to Ethanol with Selected Yeast Strains and B-Glucosidase Supplementation", Applied Biochemistry and Biotechnology, 1989, vol. 20/21, pp. 529-540.

Spindler, Diane, Wyman, Charles and Grohmann, Karel; "Evaluation of Pretreated Herbaceous Crops for the Simultaneous Scaccharification and Fermentation Process", Applied Biochemistry and Biotechnology, 1990, vol. 24/25, pp. 275-286.

Yang, Bin, Boussaid, Abdel, Mansfield, Shawn D., Gregg, David J. and Saddler, John N., "Fast and Efficient Alkaline Peroxide Treatment to Enhance the Enzymatic Digestibility of Steam-Exploded Softwood Substrates", Biotechnology and bioengineering, Mar. 20, 2002, vol. 77, No. 6, pp. 678-684.

(Continued)

*Primary Examiner*—Anish Gupta
(74) *Attorney, Agent, or Firm*—Lathrop & Gage LLP

(57) ABSTRACT

Disclosed is a method for converting cellulose in a lignocellulosic biomass. The method provides for a lignin-blocking polypeptide and/or protein treatment of high lignin solids. The treatment enhances cellulase availability in cellulose conversion. Cellulase efficiencies are improved by the protein or polypeptide treatment. The treatment may be used in combination with steam explosion and acid prehydrolysis techniques. Hydrolysis yields from lignin containing biomass are enhanced 5-20%, and enzyme utilization is increased from 10% to 50%. Thus, a more efficient and economical method of processing lignin containing biomass materials utilizes a polypeptide/protein treatment step that effectively blocks lignin binding of cellulase.

20 Claims, 3 Drawing Sheets

OTHER PUBLICATIONS

Sewalt, V.J.H., Glasser, W.G. and Beauchemin, K.A., "Lignin Impact on Fiber Degradation. 3. Reversal of Inhibition of Enzymatic Hydrolysis by Chemical Modification of Lignin and by Additives", J. Agric. Food Chem, 1997, vol. 45, No. 5, pp. 1823-1828, American Chemical Society.

Mohagheghi, A., Tucker, M., Grohmann, K. and Wyman, C., "High Solids Simultaneous Saccharification and Fermentation of Pretreated Wheat Straw to Ethanol", Applied Biochemistry and Biotechnology, 1992, vol. 33, pp. 67-81, The Humana Press Inc.

Lu, Yanpin, Yang, Bin, Gregg, David, Saddler, John N. and Mansfield, Shawn D., "Cellulase Adsorption and an Evaluation of Enzyme Recycle During Hydrolysis of Steam-Exploded Softwood Residues", Applied Biochemistry and Biotechnology, 2002, vol. 98-100, pp. 641-654, Humana Press Inc.

Eriksson, Tony, Borjesson, Johan and Tjerneld, Folke, "Mechanism of surfactant effect in enzymatic hydrolysis of lignocellulose", Enzyme and Microbial Technology 2002, v. 31, pp. 353-364, Elsevier Science Inc.

Torget, R., Himmel, M. and Grohmann, K.; "Dilute-Acid Pretreatment of Two Short-Rotation Herbaceous Crops", Applied Biochemistry and Biotechnology, 1992, vol. 34/35, pp. 115-123, The Humana Press Inc.

Sutcliffe, Roger and Saddler, John N., "The role of Lignin in the Adsorption of Cellulases during Enzymatic Treatment of Lignocellulosic Material", Biotechnology and Bioengineering Symp. No. 17, 1986, pp. 749-762.

Wu, Michael M., Chang, Kevin, Gregg, David J., Boussaid, Abdel, Beaston, Rodger P. and Saddler, John N. "Optimization of Steam Explosion to Enhance Hemicellulose Recovery and Enzymatic Hydrolysis of Cellulose in Softwoods", Applied Biochemistry and Biotechnology, 1999, vol. 77-79, pp. 47-54, The Humana Press Inc.

Grohmann, K., Torget, R. and Himmel, M., "Dilute Acid Pretreatment of Biomass at High Solids Concentrations", Biotechnology and Bioengineering Symp. No. 17, 1986, pp. 135-151.

Chernoglazov, Vladimir M., Ermolova, Olda V. and Klyosov, Anatole A., "Adsorption of high-purify endo-1,4-β-glucanases from *Trichoderma reesei* on components of lignocellulosic materials: cellulose, lignin, and xylan", Enzyme Microb. Technol., 1988, vol. 10, August, pp. 503-507.

Boussaid, Abdel, Robinson, Jamie, Cai, Yi-Jin, Gregg, David J. and Saddler, John N., "Fermentability of the Hemicellulose Derived Sugars from Steam-Exploded Softwood (Douglas Fir)", Int'l Conf. Biotechnol. Pulp Pap. Ind., $7^{th}$, 1998, pp. C239-C242.

Gould, Michael J., "Alkaline Peroxide Delignification of Agricultural Residues to Enhance Enzymatic Saccharification", Biotechnology and Bioengineering, 1984, vol. XXVI, pp. 046-052, John Wiley & Sons, Inc.

Ghose, T.K., Roychoudhury, P.K. and Ghosh, P., "Simultaneous Saccharification and Fermentation (SSF) of Lignocellulosics to Ethanol Under Vacuum Cycling and Step Feeding", Biotechnology and Bioengineering, 1984, vol. XXVI, pp. 377-381, John Wiley & Sons, Inc.

Overend, R.P. and Chornet, E., "Fractionation of Lignocellulosics by Steam-Aqueous Pretreatments", Philosophical Transactions of the Royal Society of London, Series A, Mathematical and Physical Sciences, Apr. 30, 1987, vol. 321, issue 1561. Technology in the 1990s: Utilization of Lignocellulosic Wastes, pp. 523-536, The Royal Society.

Schwald, W., Smaridg, T., Chan, M., Breuil, C. and Saddler, J.N., "The influence of $SO_2$ impregnation and fractionation on product recovery and enzymic hydrolysis of steam-treated sprucewood", 1989, pp. 231-242 Goughlan, M.P., Elsivier, N.Y.

Kadla, John F., Chang, Hou-Min, and Jameel, Hasan, "The Reactions of Lignins with High Temperature Hydrogen Peroxide". Holzforschung. 1999, vol. 53, No. 3, pp. 277-284, Walter de Gruyter, Berlin—New York.

Brooks, Ronald E. and Bellamy, W. Dexter, "Bioconversion of Plant Biomass to Ethanol", Proc. Annu. Fuels Biomass Symp., $2^{nd}$, 1978, pp. P-513-P-536.

Boussaid, A., Jarvis, J., Gregg, D.J. and Saddler, J.N., Optimization of Hemicellulose Sugar Recovery from a Steam-Exploded Softwood (Douglas Fir), Proc. Biomass Conf. of the Americas, $23^{rd}$, Montreal, Aug. 24-29, 1997, pp. 873-881.

Office Action dated Sep. 11, 2007 issued in related U.S. Appl. No. 11/229,817.

International Search Report and Written Opinion dated Jul. 27, 2005 issued in related PCT Patent Application Serial No. PCT/US2004/008730.

Lenauer. English Translation of EP0258575A2, May 25, 1988.

\* cited by examiner

LIGNIN-BLOCKING TREATMENT OF BIOMASS AND USES THEREOF

GOVERNMENTAL INTEREST

The United States Government may have certain rights in the present invention as research relevant to its development was funded by United States Department of Energy (DOE) contract number DE FC36-00GO010589 and DE FC36-01GO11075.

BACKGROUND OF THE INVENTION

1. Field of the Invention

The present invention pertains to the field of biomass processing to produce fuels, chemicals and other useful products and, more specifically, to saccharifying lignocellulosic biomass materials to produce sugars for conversion to ethanol and other products by enhancing the effectiveness of cellulase through selective binding or blocking of the lignin component. Use of a protein wash enhances bioconversion efficiency by increasing the availability of cellulase and other enzymes to cellulose.

2. Description of the Related Art

Cellulosic biomass is useful for generating ethanol. Such materials specifically known as lignocellulosic materials, or biomass, (e.g. wood and solid wastes), have been used as source material to generate carbohydrates, which in turn may be used to produce ethanol, as well as other products.

Lignocellulosic biomass is a complex structure of cellulose fibers wrapped in a lignin and hemicellulose sheath. The ratio of the three components varies depending on the type of biomass. Typical ratios are as follows:

TABLE 1

|  | SOFTWOODS | CORN COBS | RDF* | CORN STOVER |
|---|---|---|---|---|
| CELLULOSE | 42% | 40% | 52% | 37% |
| HEMICELLULOSE | 25% | 36% | 26% | 22% |
| LIGNIN | 28% | 13% | 20% | 17% |
| OTHER | 5% | 11% | 2% | 24% |

*RDF - REFUSE DERIVED FUEL FROM MUNICIPAL WASTE SYSTEMS

Table 1 is only an approximation. For example, wood differs in composition, depending on the particular type of wood, where softwoods, (gymnosperms) generally have more glucommanans and less glucuronoxylans than do hardwoods.

Cellulose is a polymer of D-glucose monomer with $\beta$-1-4-linkages between each monomer forming chains of about 500 to 10,000 D-glucose units. Hemicellulose is a polymer of sugars, primarily D-xylose with other pentoses and some hexoses, also with $\beta$-1-4-linkages. Lignin is a complex random polyphenolic polymer. Lignocellulose biomass represents an inexpensive and readily available substrate for the preparation of sugars. These sugars may be used alone, fermented to produce alcohols and industrial chemicals, or chemically converted to other compounds.

Ethanol is one of the alcohols that may be produced using carbohydrate derived from a lignocellulosic biomass, and has a number of industrial and fuel uses. Of particular interest is the use of ethanol as a gasoline additive that boosts octane, reduces pollution, and partially replaces gasoline in fuel mixtures. Ethanol-blended gasoline formulations are well-known commercial products commonly called "gasohol". It has been proposed to eliminate gasoline almost completely from the fuel and to burn ethanol in high concentrations.

Conversion of cellulose biomass into renewable fuels and chemicals often involves chemical and/or enzymatic treatment of the biomass with cellulase or other enzymes. In particular, cellulase enzymes hydrolyze cellulose to D-glucose, which is a simple sugar. In high lignin content lignocellulosic biomass, high doses of cellulase are needed to degrade the cellulose with high yields because the lignin binds preferentially with the cellulase, thereby reducing access of cellulase to cellulose. Consequently, when processing high lignin content biomass materials, less cellulase is available to degrade cellulose because the lignin coating of the cellulose fibers scavenges cellulase. Thus, the effectiveness of the process for digesting cellulose is reduced.

Bioconversion of cellulose biomass to ethanol has been studied since the 1940's. However, the cellulose-to-ethanol process is not yet economical compared to producing petroleum products by existing technology. Enzymatic hydrolysis is a fairly slow process. The costs of cellulases are high, and the required amount of cellulases is also high, which increases processing costs. Reduction in the amount of cellulase needed to obtain a satisfactory sugar yield can have a significant impact on process economics. Therefore, improving the efficiency of enzyme use is a major need in the bioconversion process.

The mechanism of hydrolysis and the relationship between the structure and function of various cellulases have been extensively studied. Several factors are thought to influence enzymatic hydrolysis of cellulose. These factors include lignin content, hemicellulose content, acetyl content, surface area of cellulose and cellulose crystallinity. It is generally understood that the lignin present in complex substrates, such as steam-exploded wood, especially softwoods, has a negative effect on cellulase activity. The exact reasons are poorly understood because the complexity of biomass is such that reducing one barrier to digestion can enhance or disguise the importance of others. For example, cellulose hydrolysis has been shown to improve with increasing lignin removal, although differences are reported in the degree of lignin removal needed.

A variety of factors may be associated with the deleterious effects of lignin upon saccharification. The ratio of syringyl moiety to guaiacyl moiety in the lignin may affect saccharification. Although the exact role of lignin in limiting hydrolysis has been difficult to define, it is probable that one of the most significant limitations is the effect of lignin on fiber swelling and its resulting influence on cellulose accessibility. The removal of lignin increases accessibility of cellulose and allows more cellulase activity. Lignin complexes may be physically and chemically resistant to enzyme attack. While some lignin components are water soluble, others are insoluble and may precipitate from solution. Condensed lignin has the ability to adsorb protein from aqueous solutions. Lignin removal may open more surface area for enzymatic attack and reduce the amount of cellulase that is non-specifically adsorbed on the lignocellulosic substrate. Studies involving acid pretreated softwood report a positive correlation between digestibility and the extent of delignification, but the results are complicated by the presence of hemicellulose. Some substrates require higher temperatures for hemicellulose removal to be effective, suggesting that hemicellulose is not the only additional factor impacting digestibility, and other evidence does not support a role for hemicellulose in changing cellulose digestibility.

Although cellulose crystallinity is generally reasoned to impede enzymes, rates slow with increasing crystallinity in some studies, but increase in other studies. The degree of crystallinity may not significantly change over an extended hydrolysis time. Crystallinity seems less important than lignin removal and to impact rates more than yields. Several studies have focused on explaining cellulose digestibility by the accessibility of cellulose to enzymes. Correlations have been developed to relate rates to pore volume and accessible surface area. However, the complex shape of cellulases may create difficulty in penetrating such pores, and concerns have been raised about substrate changes during these measurements.

Cellulases are composed of a mixture of enzymes having different activities, and the enzyme structure differs between microorganisms. While the mechanisms of hydrolysis and the relationship between the structure and function of various cellulases have been extensively studied, many details of enzymic activity are still poorly understood. The enzymatic hydrolysis of cellulose substrates is strongly affected by end-product inhibition and enzyme features. Low specific cellulase activity on cellulose is an important factor that limits the effectiveness of hydrolysis. One way to circumvent this low specific activity is to recycle and reuse the enzyme. However, non-productive cellulase adsorption plays an important role in the development of ways to reuse enzymes and affects recycle efficiency.

Besides the complexity of the different types of cellulases, activity on the substrate is also complicated by substrate characteristics. Due to resistance from the complex structure and composition of natural cellulosic biomass, the lignocellulose substrate should be pretreated to make it as susceptible as possible to the action of the enzymes. Many pretreatment methods have been developed. For example, increased accessibility of lignocellulose substrate can be achieved by solubilizing hemicellulose in harsh acidic conditions.

Cellulase adsorption on lignocellulosic substrates containing high content of natural materials has not been extensively studied. Typically, lignocellulosic substrates contain a much higher content of lignin compared to "model" cellulose substrates. Lignin may inhibit enzymatic hydrolysis of lignocellulosic material. Cellulases are not only adsorbed to the cellulosic part of the substrate, but also adsorbed to the lignin. Lignin not only shields the cellulose but also acts as a competitive adsorbent. However, lignin does not appear to restrict the extent of hydrolysis of the carbohydrate moiety if sufficient cellulase is present. Cellulolytic enzymes bind strongly to lignin. When adsorption profiles are compared, much more enzyme protein is associated with hydrolyzed residues of lignocellulosic materials than that of model cellulose. β-glucosidase has a high affinity for various lignin fractions, while it does not bind to polysaccharides. The irreversible adsorption of specific cellulase components is not observed in the prolonged hydrolysis of steamed shirakamba wood containing abundant lignin. It is unclear whether the adsorption of cellulases on lignin results from specific or non-specific binding. When the lignin is extracted from a steam-exploded aspen wood with water and alkali prior to hydrolysis, cellulases is still found to be adsorbed to the lignin.

Lignin plays an important role in enzymatic hydrolysis of lignocellulosic material, as reported in Sutcliffe & Saddler, Biotechnol. *Bioeng. Symp.* $8^{th}$, 17:749-62 (1986). Comparative adsorption profiles demonstrate that much more enzyme was retained with hydrolyzed residues, compared to that of model pure cellulose, as reported in Abdel & Saddler, Int. Conf. Biotechnol. Pulp Pap. Ind., $7^{th}$, C239-C242 (1998). In a study by Chernoglazov et. al., Enzyme Microb. Technol., 10:503-507 (1988), endoglucanases that adsorbed on lignin lost activity. The inactivating effect of lignin was observed also with steam-exploded substrate, but not if the latter was acid-treated, nor with the lignocarbohydrate complex. Sutcliffe et al., Biotechnol. Bioeng., 17: 749-762 (1986) report that adsorption of cellulases on different lignin preparations from steam-treated hardwood is influenced by the nature of the lignin and β-glucosidase was most affected by lignin. Thus, different types of lignin and forms of lignin may influence cellulase adsorption. Also, the form of the lignin, which contains distinct lignin and lignocarbohydrate complexes, seems to influence cellulases differently. It is generally agreed that the form and positioning of most lignin changes after steam-explosion, such that the lignin separates from cellulose to form agglomerates.

Several proposals have been made for solving the problem of ineffective and/or inefficient enzyme degradation of high lignin containing biomass materials. One of these is a pretreatment step that degrades or removes at least a portion of the hemicellulose and/or lignin from the biomass. For example, a combination of heat and acid pre-treatment of the lignocellulosic mass for a period of time has been used to hydrolyze hemicellulose. However, this process provides for only very limited removal of lignin, as reported in Grohmann et. al. Biotechnol. Bioeng. Symp. 17, Symp. Biotechnol. Fuels Chem., $8^{th}$, 135-151 (1986) and Torget et al., Applied Biochemistry and Biotechnology, 34-35:115-123 (1992).

Lignin removal from cellulosic fibers has also been proposed though using a caustic alkali, such as in Kraft pulping and paper making. However, this process does not produce simple sugars and does not separate the hemicellulose from the cellulose.

U.S. Pat. No. 4,668,340 issued to Sherman relates to biomass hydrolysis processing that produces almost exclusively hemicellulose sugars. Acid is introduced to the biomass, and is removed from each stage to be fed to the next in its sequence. The hydrolysis of cellulose is minimized in the process, and results in a cellulosic pulp containing over 90% of the feed α-cellulose.

U.S. Pat. No. 4,708,746 issued to Hinger relates to the specific hydrolysis of cellulose followed by treatment with high-pressure steam. However, the use of high steam alone does not provide for the complete hydrolysis of the cellulose substrate.

U.S. Pat. No. 5,125,977 issued to Grohmann et al., and U.S. Pat. No. 5,424,417 issued to Torget et al., relate to the prehydrolysis of a lignocellulosic biomass to solubilize the hemicellulosic sugars with concomitant release of some soluble lignin. Prehydrolysis renders the remaining cellulose more readily digestible with enzymes or other chemical means. U.S. Pat. No. 5,424,417 describes a process wherein lignocellulose is subjected to a prehydrolysis step by passing an acidic or alkaline solution through solid or lignocellulosic particles, with the continuous removal of soluble reaction products. The technique permits a less severe combination of pH, temperature, and time than conventional prehydrolysis. Extraction of hemicellulose and lignin occurs simultaneously in the same reactor and under the same conditions.

U.S. Pat. No. 6,022,419 issued to Torget et al. relates to a process in which a lignocellulosic biomass is fractionated by using a dilute acid, e.g., dilute sulfuric acid at 0.07 wt %, to convert cellulose into monomeric sugars in relatively high yields. However, cellulose hydrolysis using an acid catalyst is costly and requires special equipment. In addition, the desired sugars are labile to the harsh conditions, and significant amounts of unwanted and toxic by products typically form. If exposed too long, the glucose derived from the cellulose degrades into hydroxymethylfurfarol, which further degrades into unwanted degradation products including levulinic acid and formic acid. The acidic conditions similarly degrade xylose, which is formed from hemicellulose.

WO 9429474 issued to Hinman relates to a process in which a treatment of lignocellulose minimizes binding of cellulase. A substrate is formed of cellulose, hemicellulose, and starch. A hydrolytic acid pretreatment agent is added to the substrate, as is a lignin peroxidase to block lignin binding sites in the biomass. Cellulase is added to the substrate using Simultaneous Saccharification and Fermentation (SSF) process conditions favorable for cell viability and conversion of ethanol.

Kadal et al., 53: 277-284 (1999) relates to the use of peroxide treatments to remove lignin under alkaline conditions during pulp bleaching. Under alkaline conditions, hydrogen peroxide reacts with both aliphatic and aromatic structures of lignin, leading to depolymerization and subsequent removal with water washing. Gould, Biotechnol. Bioeng., 26:46-52 (1984), reports the use of alkaline peroxide to remove lignin and improve enzymatic hydrolyzability of herbaceous residues. Ramos et al., Holzforschung 46:149-154 (1992), report the use of alkaline peroxide to steam explode hardwood. Yang et al., Biotechnology and Bioengineering 77(6): 678-684 (2002), report the use of alkaline peroxide treatment to enhance the enzymatic digestibility of steam-exploded softwood substrates.

Generally, softwoods have been considered the worst-case scenarios as a feedstock for the bioconversion processes because their highly recalcitrant lignin reduces the efficiency of enzymatic hydrolysis. Schwald et al., Enzyme Systems for Lignocelluosic Degradation, Goughlan, M. P., Elsivier, N.Y., pp. 231-242 (1989), and Wu et al., Appl. Biochem. Biotechnol., 77-79, 47-54 (1998), report that a compromise in the pre-treatment conditions will likely be required, if softwood residues are to be considered as a potential feedstock for biomass processing, i.e., a medium severity process is needed between those optimized for high hemicellulose recovery and efficient cellulose hydrolysis.

According to the aforementioned pretreatment processes, cellulose substrates produced by pretreatment at medium severity (about log $R_0$=3.76) contain a high lignin content that limits cellulase accessibility to cellulose. The term "$R_0$" is used in the industry as an indicator of the relative severity of a treatment method for the processing of a biomass. Specifically, in the field of lignocellulosics and fractionation of wood components, "$R_0$" has been used to define a "severity parameter." This equation is described in Overend, R. P. & Chornet, E. (1987 Fractionation of lignocellulosics by steam-aqueous pretreatments. *Phil. Trans. R. Soc. Lond.*, 523-36.):

$$R_0 = t \cdot \exp[(T-100)/14.75] \tag{1}$$

where $R_O$ is the severity factor and is optimized at 3.8 for the prehydrolysis of hemicellulose, t is time of exposure in minutes, and T is temperature in degrees Centigrade.

SUMMARY OF THE INVENTION

The present invention advances the art and overcomes the problems outlined above by providing an improved and more efficient method for enzymatically hydrolyzing high lignin-content biomass. These advantages are obtained without necessarily subjecting the biomass to harsh or other reaction conditions and, further, by a process that avoids significant production of toxic and unwanted degradation by-products.

In one embodiment, the method utilizes a protein and/or polypeptide that preferentially binds with lignin more readily than cellulose. A high lignin-content biomass is treated with the liginin blocking protein and/or polypeptide, for example by washing the biomass with a composition that comprises the lignin-blocking protein and/or polypeptide or by adding such materials to a saccharification broth. The lignin-blocking polypeptide and/or protein preferentially bind and thereby impede the lignin from further binding. Cellulose-hydrolyzing enzymes, such as cellobiohydrolase and β-glucosidase, may then hydrolyze cellulose more efficiently and rapidly. Without treatment of the lignin-containing biomass with a lignin-blocking polypeptide and/or protein, lignin in the biomass irreversibly binds a portion of the cellulose hydrolyzing enzymes, rendering them unable to hydrolyze cellulose. Protein and/or polypeptide treatment effectiveness through lignin binding, thus reducing and/or eliminating nonproductive adsorption of the enzymes. The treatment of biomass with a lignin-blocking protein and/or polypeptide thus improves processing of relatively high lignin substrates by circumventing affinity of lignin for the enzymes. The polypeptide wash reduces enzyme use and/or improves performance because the enzymes do not become bound to the lignin, and remain available to hydrolyze the biomass.

In one aspect, the present method reduces enzyme loading in hydrolysis of high lignin content biomass. The amount of enzyme, such as cellulase, that is needed to provide hydrolysis is significantly reduced through treating the biomass with a lignin-blocking protein and/or polypeptide. These advantages reduce the overall costs of biomass conversion processes.

According to one embodiment, the method enhances the enzymatic digestibility of cellulose. This method includes the steps of treating a high lignin biomass with a lignin-blocking polypeptide and/or protein to provide a treated biomass having a blocked lignin component, and exposing the treated biomass to an effective amount of a hydrolyzing enzyme. By way of example, the hydrolyzing enzyme comprises β-glucosidase, cellobiohydrolase, endoglucanase, or a combination thereof.

Lignin-blocking polypeptides and/or proteins that are useful for these purposes include any polypeptide and/or protein, or lignin-blocking fragment thereof, having an affinity for lignin, and especially, for example, bovine serum albumin (BSA), soybean protein, amylase, chicken egg albumin, and combinations thereof. Lignin-blocking polypeptides and/or proteins may be any polypeptide or protein that does not have appreciable binding affinity for cellulose. By way of example, lignin-blocking polypeptides and/or proteins may have a molecular weight ranging from 2,000 Daltons to 300,000 Daltons. In some embodiments, the range may be that of a relatively high molecular weight, ranging from 55,000 Daltons to 80,000 Daltons, e.g., that of an albumin. However, lignin-blocking polypeptides and/or proteins having a lower molecular weight are also envisioned as useful in the practice of the present methods. These smaller lignin-blocking polypeptides, for example, may comprise a peptide fragment comprised of amino acids that is capable of effectively blocking or otherwise interfering with binding sites on the lignin.

The lignin-blocking materials, such as polypeptides, proteins, and fragments thereof, are not molecules that are otherwise intrinsically available to a lignin-containing biomass. The lignin-blocking materials are usually provided in a relatively purified and isolated preparation of such materials, and in concentrations that are not present in nature. Thus, an incidental presence of protein and/or peptide, e.g., in a saccharification or fermentation media, would not provide the lignin-blocking action of the herein defined preparations. The lignin-blocking polypeptides, proteins and/or lignin-blocking fragments thereof are provided to the biomass as an externally supplied source of material not inherent to the native milieu of a biomass under ordinary circumstances, absent intervention by the hand of man.

The lignin-blocking polypeptides and proteins may be prepared in a composition with water, for example. The lignin-blocking polypeptide or protein that is used in the treating step may include a relatively low concentration of lignin-blocking polypeptide and/or protein, for example, 1% of the lignin-blocking polypeptide and/or protein by weight of the composition, or from 1% to 5% by weight of the composition.

The methodology employs compositions of a lignin-blocking polypeptide and/or protein, as well as composition of a cellulose hydrolyzing enzyme, such as cellulase. As used here, a composition is defined as including a colloidal suspension, liquid phase of a mist, liquid/solid mist suspensions, vapor mixtures, and/or a solution that includes the lignin-blocking protein and/or polypeptide or a lignin-blocking fragment thereof.

Lignin is a phenolic polymer that can be derived by the dehydrogenative polymerization of coniferyl alcohol and/or sinapyl alcohol. Lignin has water-soluble and non-water soluble forms. Both water-insoluble and water-soluble lignins absorb polypeptide and protein. Lignin presents non-specific adsorption sites for polypeptide and protein binding with, for example, lignin-treating polypeptides and proteins like bovine serum albumin and chicken egg albumin. Condensed lignin has the ability to absorb polypeptide and protein from aqueous solutions. Dihydroxyphenyl groups and phenolic hydroxyl groups of the lignin molecule form binding sites that may be used to bind with and/or precipitate protein. Many different proteins can, therefore, be used to bind lignin and enhance enzyme access to cellulose in a biomass.

By way of example, a lignocellulosic biomass having high lignin content is defined as a biomass that comprises at least 5% by weight lignin, at least 10% by weight lignin, at least 20% by weight lignin, at least 40% by weight lignin, from 5% to 50% lignin, or from 10% to 50% by weight lignin. Process conditions for hydrolyzing cellulose are, generally, a temperature ranging from about 120° C. to 240° C., a pressure ranging from about 12 psig to about 470 psig, and acid concentration ranging from 0 to 5% by weight.

In various embodiments, the lignocellulosic biomass comprises wood, agricultural and forestry residues, grasses, municipal wastes (paper mill effluent, newspaper, cardboard, etc.), or combinations thereof. For example, the lignocellulosic material may comprise birch, Douglas fir, corn stover, straw, or a combination thereof. These materials may be subjected to other preprocessing that decreases or increases their lignin content, for example, effluent from a paper mill. Thus, the method is applicable to environmental remediation processes, as well as those intended to produce ethanol from fuel. The lignin-blocking polypeptide and/or protein treatment of a biomass may occur simultaneously with the addition of a cellulose-hydrolyzing enzyme to the biomass. A lesser advantage in conversion efficiency may be provided. It is envisioned however, that first treating a biomass with a lignin-blocking polypeptide and/or protein, or lignin-blocking fragment thereof, and then adding the cellulose hydrolyzing enzyme provides the most efficiency in cellulose conversion.

Treating a biomass with a lignin-blocking polypeptide and/or protein, e.g., by washing with a protein solution, may be followed by adding cellulase, or an enzyme of similar cellulose hydrolyzing activity. This treating step produces a hydrolysis yield from the cellulose that may be measured as percentage improvement in cellulase conversion efficiency. By way of example, a 20% improvement in percentage conversion of the total cellulose to carbohydrate may be obtained in comparison to the hydrolysis yield from cellulose of a biomass that is not treated with a lignin-blocking polypeptide and/or protein. As used herein, the term "a lignin-blocking polypeptide and/or protein" means any protein capable of providing a comparative improvement in cellulase conversion efficiency by binding with lignin to increase the availability of hydrolyzing enzyme. Saccharification of high lignin content substrates often benefits by at least a 5% improvement in conversion efficiency.

Still other embodiments pertain to improved processes for producing an organic compound from a high lignin-containing lignocellulosic biomass. The washing or lignin-blocking polypeptide and/or protein treating step may be preceded, for example, by a hydrolyzing step of contacting the lignocellulosic biomass with acid and steam to provide a treated solid biomass with a greater lignin component. The hydrolyzed biomass is then washed and treated with a lignin-blocking polypeptide and/or protein. This lignin-blocking treatment is followed by adding an effective amount of a hydrolyzing enzyme under conditions that are suitable for hydrolysis of the cellulose to produce carbohydrate at an efficient high rate. The effective amount of hydrolyzing enzyme for a lignin-blocking polypeptide and/or protein-treated biomass, for example, is at least 25% less than the effective amount of hydrolyzing enzyme required for a similar conversion yield from a lignocellulosic biomass that is not treated with lignin-blocking polypeptide and/or protein.

Process steps in addition to the hydrolyzing step or steps may include extracting the carbohydrate, fermenting the carbohydrate in the presence of an ethanol-converting microorganism for a period of time and under suitable conditions in a reaction mixture for producing ethanol and extracting the ethanol from the reaction mixture. Extraction may occur, for example, by ultrafiltration and/or fractional distillation. Cellulase-performance measured as a minimum cellulase concentration required to achieve a time-to-target cellulose conversion are improved from 5% to 75%, or from 20% to 75%, measured as a percentage difference compared to other processes that do not provide for a lignin-blocking protein and/or polypeptide treatment of the biomass.

Additional embodiments of the method comprise mixing particulate biomass having a high lignin content with a sufficient amount of an aqueous acid to produce a wet meal of lignocellulosic biomass, heating the biomass to remove hemicellulose, cooling and washing the solid, introducing a sufficient amount of a lignin-blocking polypeptide and/or protein to the residual solids to produce a treated biomass with a blocked lignin component, and adding an effective amount of a hydrolyzing enzyme to the treated biomass to provide carbohydrate.

Substrates pretreated under higher severity are more accessible to cellulase enzyme, but have lower recovery of the hemicellulose-derived sugars. By contrast, pretreatment at lower severity conditions generally liberates hemicellulose-derived sugars, but generate a solid residue that is not readily amenable to the hydrolysis of cellulose.

Primarily, adding protein in the cellulase solution can increase stability and prevent denaturation of cellulase. This effect in lignocellulose hydrolysis is explained by the protein's ability to block the non-specific adsorption sites of non-cellulose fraction of the substrate and enhance the amount of cellulase available to absorb on the cellulose fraction. Lignin affinity for cellulase may be blocked by protein in the three ways:

(1) close physical association with lignin;
(2) hydrophobic groups adsorption to lignin; and (3) precipitation involving dihydroxyphenyl groups and phenolic hydroxyl groups of lignin As to the latter mechanism, lignin is a complex phenolic polymer that may result from the dehydrogenative polymerization of coniferyl alcohol and/or sinapyl alcohol. Both water-insoluble and water-soluble lignin adsorb protein. The adsorption capacities vary depending on the different pretreatment methods and feedstocks. Furthermore, results show that added protein at low concentrations does not effect the rate of hydrolysis, which suggests that protein has no effect on the catalytic mechanism of the cellulolytic enzymes. Therefore, it is likely that protein blocks the non-specific adsorption sites on lignin to prevent unproductive binding of cellulases on lignin. The resulting improvement in hydrolysis may occur by introducing negative charges onto the lignin surface due to adsorption of protein. In turn, the negative charges prevent binding of negatively charged hydrolyzing enzymes. Without being bound by theory, it is believed that nonspecific binding of protein to lignin decreases unproductive binding of cellulases to lignin surfaces. Use of protein treatment in a process for lignocellulose conversion advantageously facilitates a lowering of the cellulase loading level to achieve the same target conversion percentage. For example, in the studies reported below, it was possible to lower the enzyme loading by 50% to achieve the same level of hydrolytic cellulose conversion with addition of protein at 2 g/L to pretreated lignocellulose substrates.

DETAILED DESCRIPTION OF THE PREFERRED EMBODIMENTS

There will now be shown and described a process for increasing process efficiency in making useful products out of high lignin content lignocellulosic biomass. Efficiency is improved by treating the biomass with a lignin-binding protein and/or polypeptide. In some embodiments, this is accomplished with a protein wash of the biomass. Protein binding to lignin renders the lignin less available to bind cellulase or other cellulose-hydrolyzing enzyme. Thus, more cellulase is available to hydrolyze cellulose in a protein-treated biomass, and less cellulase is ultimately needed to provide a higher yield of component sugars from the biomass. The process is thus much more efficient than those in the prior art. In addition, hydrolytic activity occurs with greater speed.

The following discussion provides specific instances of this process demonstrating the instrumentalities according to the various embodiments by way of example, and not by limitation.

Figure 1:
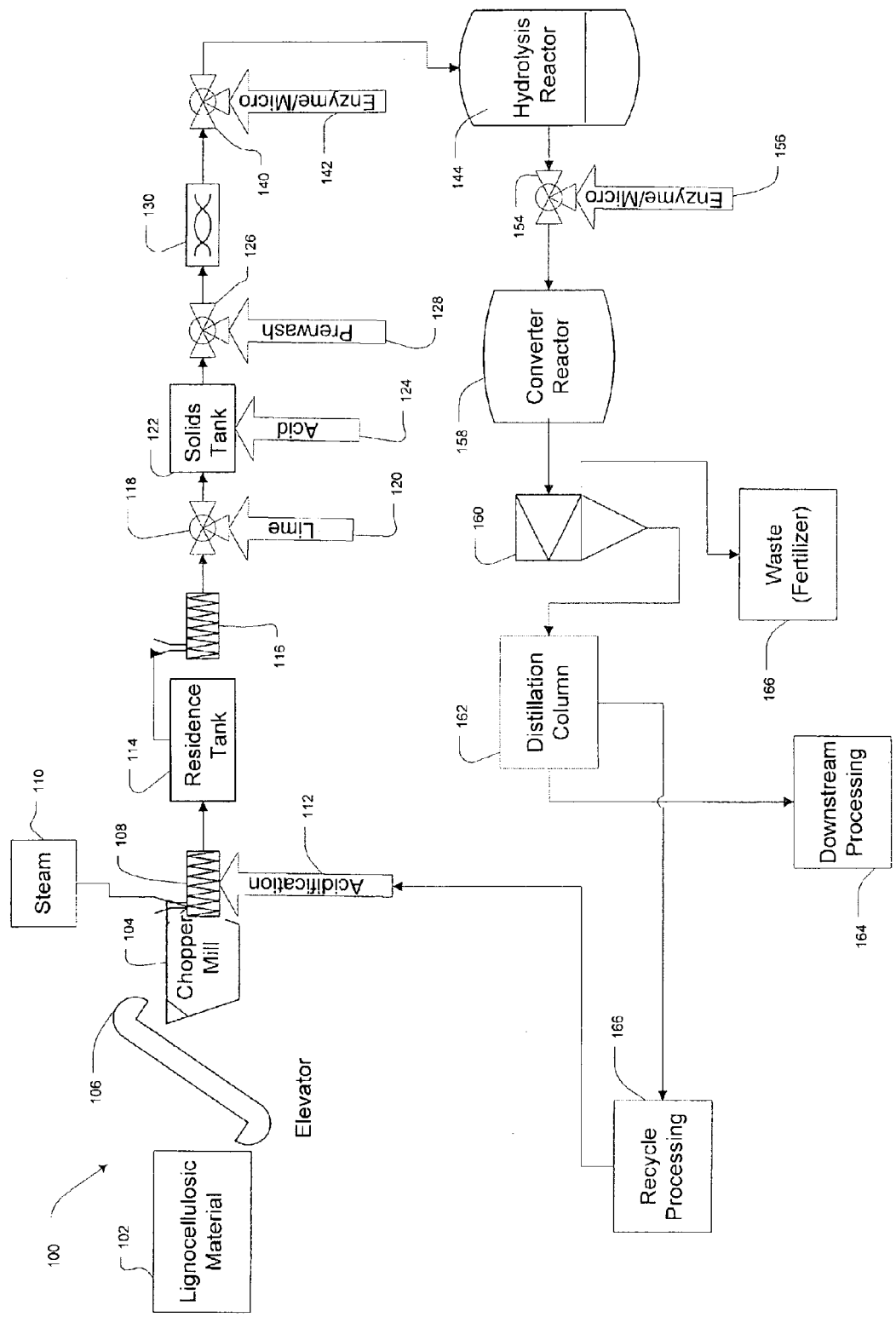
FIG. 1 is a schematic diagram showing process equipment that may be used according to one embodiment that uses BSA protein washing for lignocellulose conversion.

FIG. 1 shows one embodiment of a reactor system 100 that may be used for biomass conversion. A pile of lignocellulosic material 102 is conveyed to chopper mill 104 by the action of elevator 106. The chopper mill 104 chops and/or grinds material of the lignocellulosic biomass pile 102 to a predetermined size that is suitable for downstream processing. A screw extruder 108 transfers the chopped lignocellulosic material from chopper mill 104. Steam 110 may be added to screw extruder 108, which may be configured to produce a steam explosion in the lignocellulosic material 102, for example, by processing the lignocellulosic material at high pressure sufficient to prevent boiling and temperature of 120° C. to 240° C. for a time ranging from one minute to sixty minutes or more. The screw extruder 108 optionally slurries the chopped lignocellulosic material with an acidification solution 112 that contains, for example, from 1% to 5% by weight of sulfuric acid mixed to homogeneity in water, e.g., to produce a pH of 1.2 to 1.4. The discharge from screw extruder 108 is flashed into residence tank 114, which is maintained at a temperature below 100° C. to cool the material and stop further reaction.

Residence tank 114 discharges into a screw conveyor 116, which at a first three way mixing station 118 mixes the slurry with a lime solution 120, e.g., one with sufficient lime to impart a predetermined pH of 10 to 11. The slurry is discharged into a solids holding tank 122 where it resides for an appropriate time permitting the lime to remove deleterious byproducts of acid hydrolysis. Additional acid 124, such as sulfuric acid, may be added into the solids holding tank 122 to adjust pH into a range from 5 to 7. The solids holding tank 122 discharges into a second three way mixing station 126 for further mixing with a prewash solution 128 that contains a lignin-blocking protein and/or polypeptide, e.g., one imparting a 1% to 5% lignin blocking protein and/or polypeptide content by weight of the slurry. Further mixing occurs through turbulator 130, which discharges into a third three way mixing station 140.

In turn, the third three way mixing station 140 introduces an enzymatic solution 142 that contains a prehydrolyzing enzyme, for example, cellulase or a mixture of cellulase and other enzymes including glucosidase. Alternatively, the enzymatic solution 142 contains an inoculum and growth medium including a microorganism capable of saccharifying the slurry for hydrolysis of cellulose by the in vivo production of such enzymes. The slurry travels to a heated hydrolysis reactor vessel 144, which may be one of a series of such reactor vessels, for an appropriate residence time permitting hydrolysis of the slurry. For example, this residence time may be from one to three days. A series (not shown) of hydrolysis reactor vessels 144 may permit continuous batch processing.

Slurry discharge from the hydrolysis reactor 144 may be subjected to additional mixing at a fourth mixing station 154, which adds a second enzymatic solution 156, such as a microorganism-containing enzymatic solution or an aqueous solution with additional enzymes useful for conversion processes, i.e., the conversion of sugars into alcohols. The second enzymatic solution 156 reacts in a converter reactor 158, for example, to convert sugars into alcohol or other organic compounds. Discharge from converter reactor 158 may be submitted to a vortex separator 160, which discharges solids to waste disposal where the solids may, for example, be used as a boiler fuel. Liquids from vortex separator are submitted to distillation column 162, which concentrates useful products, e.g., ethanol, for further downstream processing 164, such as a molecular filter to remove water. Remaining liquids and/or solids from the distillation column 162 are submitted to recycle processing 166, for example, to filter fine particulates and add acid for use of such liquids as the acidification solution 114.

It will be appreciated that the equipment shown generally in FIG. 1 may be used or adapted to implement a variety of known processes. The prior processes do not include use of a wash (prewash) composition, such as a lignin-blocking polypeptide and/or protein prewash solution 128, and may be adapted for such use according to the instrumentalities described herein. The aforementioned use of the washing composition, prewash solution 128 results in significant cost reductions in the overall process of producing sugars or fermented organic compounds from high lignin content lignocellulose by reducing enzyme use.

As used herein, a biomass of lignocellulose having a "high-lignin content" is defined as a biomass having at least about 10% by weight lignin/cellulose. By way of example, such a biomass is characteristic of ground hardwood. The modification of known processes to include use of prewash solution 128 substantially improves cellulose conversion efficiency in processing high lignin content cellulose.

Among the processes for producing ethanol from lignocellulosic substrates (e.g., trees, grasses, and solid wastes) are those known as the Direct Microbial Conversion (DMC) process and the Simultaneous Saccharification and Fermentation (SSF) process. These processes can use a variety of microorganisms to convert organic material to ethanol. In the DMC method, a single microbial system both produces cellulase enzyme and produces ethanol as a fermentation product. The SSF method utilizes two biological elements, one that is based on cellulase enzyme and the other, which ferments sugar to ethanol.

As an alternative to adding cellulase in enzymatic solution 142, cellulase may be produced using a biomass fermentation process, for example, in a DMC process as described in Brooks et. al., Proc. Annu. Fuels Biomass Symp., $2^{nd}$ (1978), or an SSF process as described in Ghose et. al., Biotechnol. Bioeng., 26 (4): 377-381(1984). These processes may be used, as modified by the use of protein treatment, such as with a washing (such as a prewashing) step with a composition comprising a lignin blocking polypeptide and/or protein, according to the principles described herein. One example of an organism that is useful in converting organic matter to ethanol by way of the DMC process is *Clostridium thermocellum*. Other examples of suitable microorganisms that may be used with the DMC process option include *Fusarium oxysporum* and *C. cellulolyticum*. In addition, such organisms can be used in co-culture with *C. thermosaccharolyticum* or similar pentose-utilizing organisms such as *C. thermohydrosulfuricum* and *Thermoanaerobacter ethanoliticus*. An example of another microorganism that may be used in the practice of the claimed method according to the SSF process is *Saccharaomyces cerevisiae* (which produces ethanol).

A variety of suitable growth media for microbial digestion processes are well known in the art. Generally, a suitable growth medium is able to provide the chemical components necessary to maintain metabolic activity and to allow cell growth. One effective growth medium contains the following components per liter of water:

TABLE 2

| | |
|---|---|
| protein treated wood* | 5.0 g. |
| $NaH_2PO_4$ | 0.3 g. |
| $K_2SO$ | 0.7 g. |
| $NH_2SO_4$ | 1.3 g. |
| Yeast extract | 2.0 g. |
| Morpholinopropanesulfonic acid (MOPS) | 2.0 g. |
| Cysteine Hydrochloride | 0.4 g. |
| $MgCl_26H_2O$ | 0.2 g. |
| $CaCl_26H_2O$ | 0.1 g. |
| $FeSO_4$ | 0.1 g. |

*Prepared in a plugflow reactor at 220° C., 9 seconds residence time with 1% $H_2SO_4$ The medium noted above is set forth by way of example. Other suitable growth media may be used as well, including industrial media based on corn steep liquor.

According to other embodiments, a biomass that has been treated for enzymatic hydrolysis is further processed to produce an organic molecule, for example, in the converter reactor 158. As shown in FIG. 1, pH is altered by the lime solution 120, which may also occur downstream of positions shown in FIG. 1. Any of the known cellulases or cellulase complexes may be used in the enzymatic solutions 142 or 156. For example, cellulase digestion may be performed for one to three days at a temperature that is optimal for the cellulase employed. The sugar-containing solution is then separated from the residues, for example, by filtration, sedimentation, or centrifugation. The sugar solution may be recovered as sugars or it may ferment to produce a desired organic chemical.

According to various embodiments and instrumentalities, the lignocellulosic material 102 may be woody biomass, herbaceous biomass (e.g., forage grass), and waste material (e.g., municipal solid waste). The size range of the lignocellulosic raw material varies widely and depends upon the type of material used as well as the requirements and needs of a given process. The size of the lignocellulosic raw material particles discharging from chopper mill 104 prior to downstream processing ranges from less than a millimeter in diameter to several inches in diameter. Particle size of the lignocellulosic raw material after processing through screw extruder 116 is in the range of one to four millimeters. A preferred lignocellulosic raw material is a woody biomass material comprised of particulate hardwoods. Exemplary hardwoods include poplar, oak, maple, and birch.

As used herein a "significantly reduced amount" of cellulase or other cellulose-hydrolyzing enzyme is an amount of enzyme that is less than that required to hydrolyze a high-lignin biomass that has not been treated with a lignin-blocking polypeptide and/or protein. More specifically, the "significantly reduced amount" of hydrolyzing enzyme constitutes the difference between the amount of cellulase needed to hydrolyze at least 50% of the cellulose in a high-lignin cellulosic biomass that has been treated with a lignin-blocking protein and/or polypeptide and the amount of cellulase or other cellulose hydrolyzing enzyme needed to elicit the same amount of cellulose hydrolysis of a high-lignin cellulosic biomass that is not treated with a lignin-blocking protein and/or polypeptide. In particular embodiments, a "significantly reduced amount" of cellulose hydrolyzing enzyme is about 20% to about 50% less enzyme than is needed to hydrolyze cellulose in a lignocellulosic biomass not treated with a lignin-blocking protein and/or polypeptide. This improvement is made possible by use of the lignin blocking protein and/or polypeptide treatment composition, in this case a prewash solution, 128, shown in FIG. 1.

The lignocellulosic material is preferably ground before being submitted to downstream processing, e.g., as by use of chopper mill 104 in the reactor. If the nature of the lignocellulosic material is such that it will break down under the conditions of downstream processing, then grinding is not necessary. The particle size is not critical but hydrolysis generally proceeds faster with a smaller particle size, so an economic optimization may be reached between the costs of grinding the lignocellulosic material and the cost advantages of higher throughput. Smaller particle sizes inherently provide more surface area for cellulase to attack and degrade cellulose. On the other hand, for a given set of flow conditions, particles that are too small may form a dense mat, which is difficult for fluid to penetrate at an acceptable rate.

Appropriate particle sizes vary with the feedstock and its inherent physical properties, as well as the flow conditions. In most processes, particle sizes appropriate for ground wood are in the range of about 0.1 mm to 30 mm preferably in the range of 0.5 mm to 4 mm. Other materials may be larger or smaller depending on the particular materials, particularly those having at least one thin dimension such as paper or straw. If one relies on the effects of gravity or floatation to cause movement of the solid lignocellulosic material with respect to the liquid, then particle size may need to be adjusted appropriately to permit solid/liquid movement during hydrolysis. Optimum sizes depend on the particular lignocellulosic material used and the reactor size and construction and are readily determinable by routine empirical studies for a reactor and reactor flow conditions.

The cellulosic materials may include hardwood, grasses, softwood, waste paper and pulp, municipal wastes, agricultural wastes such as straws, corn cobs, stover, biomass of all types, etc. and mixtures thereof. The choice of cellulosic material depends upon the availability and cost of the particular cellulosic material being processed. The advantages of the present lignin-blocking polypeptide and/or protein treatment methods are most evident in cellulosic biomass having a lignin content of at least 5%, 10% or more, e.g., 11%, 12%, 15%, 17%, 20%, 24%, 25%, 30%, 35%, 40%, 45%, 50%, 60%, 70%, or more. The lignin-blocking treatment methods may also be used to process both raw and partially processed cellulosic materials having lower lignin content, e.g., 7%, 6%, 5% or less.

In some embodiments, the reactor vessels 144 and 158 generally may have a solids content of about 5% to 50%, preferably 8% to 50%, when the solids are present with the liquid at the end of the hydrolysis. The higher solids content is generally more desirable but the concentration may be limited by reactor design and the need for fluid to heat the solids. At the beginning of the hydrolysis, the solids content may range from 0% to 100% by weight, as the reactor may initially contain only the lignocellulosic solids or the fluid.

In still other embodiments, enzymatic solution 142 including cellulase is added to a pH adjusted slurry. The cellulase digests cellulose to sugars according to manufacturer's instructions for the digestion of cellulose. Any of the known cellulases, cellulase complexes, or other cellulose hydrolyzing enzymes, may be used. The digestion occurs, for example, over one to three days at a temperature optimal for the cellulase to produce a sugar-containing solution. The sugar containing solution is separated from the residues, for example, by filtration, sedimentation or centrifugation. The sugar-containing solution may be processed to recover sugar or further reacted or fermented to produce a desired organic chemical, such as an alcohol.

In fermentation processes, for example, the fermenting microorganism in second enzymatic solution 156 may be the same as was used in the enzymatic solution 142, but there may be a change in process conditions, such as a conversion from aerobic to anaerobic process conditions in the converter reactor 158. Cellulose digestion primarily produces glucose in the solids tank 122. A much wider variety of microorganisms may be used to produce an even wider assortment of organic compounds in the converter reactor 158. The residue digest may be fermented in any manner known per se to utilize glucose. If so desired, the discharge from screw extruder 116 may be separated into liquid and solid components for separate process streams and recombined at a downstream position.

As an alternative to separate cellulase digestion and fermentation, both reactions may occur concomitantly in simultaneous saccharification and fermentation processes, for example, within the hydrolysis reactor 144. Any fermentation that is operable in conditions suitable for cellulase is acceptable. The conditions and concentrations in simultaneous saccharification and fermentation (pH, temperature, etc.) may be measured and adjusted to be optimized for either saccharification or fermentation or for overall optimization. The conditions may be changed as the process progresses.

The following description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitations.

All references mentioned in this application are incorporated by reference to the same extent as though fully replicated herein. In the following examples, Laminex cellulase was purchased as Cytolase™ (a trademark of Genencor located in San Francisco, Calif.). The specific activity of the cellulase enzyme was approximately 28 international filter paper units (IFPU)/ml, as determined by National Renewable Energy Laboratory's Laboratory Analytical procedures LAP-006 (NREL, 2001). β-glucosidase was purchased as Novozyme 188 Sigma™ (a trademark of Novozyme located in Franklin, N.C.), and was used in the present preparations at a ratio of 1:1.75 (FBUase:CBUase). However, compositions of hydrolyzing enzyme that have a ratio of 1:1 to 1:10, or 1:1 to 1:2. The remaining specified by chemical name were purchased in research grade purity on commercial order from national laboratory supply houses. Cellulose powder (α-cellulose), used as a control substrate, was obtained from Sigma Chemical Co of St. Louis, Mo.

The particular ratio of the enzymes can be adjusted on a case-by-case basis, for example, to optimize the amount of needed with a particular microorganism that is being used. In some cases, no β-glucosidase may be used because of the microorganism being used.

The yeast used in the simultaneous saccharification and fermentation (SSF) Examples was *Saccharomyces cerevisiae* $D_5A$, as described in Spindler et al, Biotechnology Letters, 14: 403-407(1992).

The protein treatment composition may be prepared as a wash, such as in solution, prepared in distilled water. By way of example, one such wash solution was prepared by dissolving 10 gram (g.) of bovine serum albumin in one (1) liter (1000 mls) of distilled water. For example, where the biomass being washed has a weight of about 100 grams, the above protein washing composition would be prepared and the biomass would be washed with two liters of the described 1% BSA solution.

EXAMPLE 1

High Lignin-lignocellulosic Biomass Treatment with a Lignin-binding Protein

The present example demonstrates the utility of using a protein treatment, such as a protein/polypeptide washing step, to enhance the efficiency of cellulase activity in a high-lignin content lignocellulosic biomass. As compared to prior methods, that attempt to degrade and remove the lignin content, the present method blocks the lignin by protein binding that prevents lignin from scavenging digestion enzymes. This example compares the protein washing methodology in the form of a wash pretreatment to prior art processing with acid hydrolysis and/or steam explosion. Results show that similar efficiencies may be obtained by using substantially less cellulase enzyme when the biomass is prewashed with a protein solution that contains lignin-binding protein.

Two examples of biomass were examined. These were a biomass made from corn stover (CS) and a biomass made from Douglas fir. For each sample, chemical analysis was performed to determine beginning concentrations of cellulose, lignin and hemicellulose at the end of acid pretreatment, prior to protein washing, and prior to hydrolysis by cellulase. Cellulose content, lignin content, and hemicellulose content were determined by National Renewable Energy Laboratory's Laboratory Analytical Procedures LAP-002 & 003 (NREL, 2001).

Pretreatment of CS was with 0.1% $H_2SO_4$ at 180° C. for 40 minutes, or 0.1% $H_2SO_4$ at 160° C. for 80 minutes, as indicated in Table 3. The solid residue was washed with water (15 times by weight) to remove acidic groups before enzymatic hydrolysis.

The Douglas fir (*Pseudotsuga menziesii*) sapwood and heartwood were chipped and screened to a relatively homogeneous chip size of 4×4×1 cm. The chips were steam exploded in batches of 50 g dry weight using steam explosion conditions of 195° C., 4.5 min., and 4.5% (w/w) $SO_2$ as previously described in Boussaid et al, *Optimization of hemicellulose sugar recovery from a steam-exploded softwood*, Proceedings of the Biomass Conference of the Americas, 3rd, Montreal, Aug. 24-29, 1997). These steam explosion conditions were chosen out of 13 experimental sets that included variations at five levels of temperature, $SO_2$ content and time. They provided the best recovery of overall sugars originating from hemicellulose and cellulose. The solid residue was washed with water (15 times by weight) to remove acidic groups before enzymatic hydrolysis.

Protein washing of selected samples occurred such that conversion efficiency in samples that were pre-washed with 1% bovine serum albumin could be compared to efficiency of samples that were not prewashed with bovine serum albumin.

Protein prewashing included washing each of the samples with 1% (w/w) protein solution by filtering the solution through a medium glass filter 3 times at room temperature. The solid residue was left, which was conducted at 2% solids concentration (g dry weight/100 mL) in 50 mM acetate buffer, pH 4.8 containing 40 mg/ml tetracycline and 30 mg/mL cycloheximide. Flasks were pre-incubated at 45° C. on a rotary shaker at 150 rpm for 10 minutes. The enzymes were added to start the hydrolysis after acclimation. Aliquots of 0.5 mL were taken at different times (0, 0.2, 1, 4, 8, 12, 24, 48, 72 hour), immediately chilled on ice, and centrifuged at 5,000 g for 10 minutes. Total sugar analysis was performed on the resultant supernatants.

The enzyme preparations used for all hydrolysis studies were obtained from Genencor. Treatments were performed with a complete cellulase supplemented with β-glucosidase, (Novozyme™ 188) at a ratio of 1:1.75 m (FPUase:CBUase). Enzymatic treatments were performed at different FPUase/g cellulose. Total FPU were calculated by adding the activities of both the Celluclast™ and Novozyme™ 188. The cellulase preparation possessed 28 filter paper units (FPU)/mL, whereas Novozyme™ 188 possessed 8 FPU/mL, and 480 β-glucosidase IU/mL, and was supplemented to avoid end-product inhibition due to cellobiose accumulation.

Total protein was measured using the Bio-Rad Protein Assay using BSA as standard, as per the manufacturers specified direction. The amount of unabsorbed protein in the supernatant was reported as a percentage of the amount of protein present in the substrate blank.

The sugar content of solids and acid insoluble lignin were determined using the Klason lignin procedure published by the National Renewal Energy Laboratory's Laboratory Analytical Procedures LAP-002 &003 (NREL, 2001). Approximately 300 mg of sample was ground to pass through a 40-mesh screen from the U.S. standard sieve series, available from Central Scientific of Ohio, weighed to the nearest 0.1 mg, and placed in 10 mL reaction tubes, which were then placed in a water bath, namely the Water bath Shaker 3540™ from Apogen Technology of Melrose Park, Ill. The tubes were maintained at 30±1° C. for 1 hour with frequent stirring. The tubes were emptied into 250 ml Erlenmeyer flasks containing 84 ml. of deionized water, resulting in a 4% acid solution. These flasks were covered with aluminum foil and weighed before autoclaving at 120° C. for 1 hour. Following autoclaving, the weight loss was determined and readjusted by adding an appropriate amount of deionized water before vacuum filtering the mixture through a medium crucible. The solid residue was washed with 225-ml. of hot water to remove any remaining acid. The crucible and total acid insoluble residue (not including ash) were baked in an oven at 105° C. for 12 hours. The weight of the remaining solids divided by the initial weight of the starting material gave the fraction of acid insoluble residue, which is typically designated as the Klason lignin content.

The sugar compositional analysis of all biomass solid and liquid samples was carried out by standard analytical procedures defined by National Renewal Energy Laboratory's Laboratory Procedures, LAP -001,002,003,005 & 012(NREL, 2001). The filtrate from the acid insoluble residue test described above was on a high performance liquid chromatography system, namely a Waters 2695™ from Waters of Milford, Mass., equipped with a pulsed refractive index detector (Waters 2410™ differential refractive) to obtain sugar compositions. Filtered liquid samples from hydrolysis were also run by this method. A mixed sugar solution of known composition of arabinose, galactose, glucose, mannose, and xylose was treated in parallel by exactly the same sequence as described in the acid insoluble residue procedure to estimate the sugar loss correction factor for acid hydrolysis and autoclaving. The filtrate samples were filtered through 0.2 µm NM filters obtained from Fisher of Pittsburgh, Pa., and a volume of 20 µL was charged to the sample vials that were then loaded into the high performance liquid chromatography system equipped with a pulsed refractive index detector to obtain sugar content. The column was equilibrated with de-ionized water at a flow rate of 0.6 mL/min. Aminex HPX-87P™ columns from Bio-Rad of Sunnyvale, Calif. were used for determination of sugar content.

Table 3 provides a comparison of various digestions that were performed on specified biomass materials. In some instances, the digestions were performed without a protein prewash.

TABLE 3

Increased Cellulase Efficiency Through Use of Protein Treatment with Bovine Serum Albumin (BSA)

| FEED | Pretreatment Condition | Protein Prewash | Beginning Cellulose Content | Beginning Lignin content | Beginning Hemicellulose Content | Cellulase Applied (FPU/g cellulose) | Percent Conversion of Total Cellulose |
|---|---|---|---|---|---|---|---|
| Corn Stover | 0.1% $H_2SO_4$, 180 C., 40 min | None | 62.7 | 28.3 | 7.7 | 20 | 51.8 |
| | | 1% Protein (BSA) | | | | 12 | 50.9 |
| Corn Stover | 0.1% $H_2SO_4$, 180 C., 80 min | None | 71.7 | 24.7 | <0.5 | 20 | 47.3 |
| | | 1% Protein (BSA) | | | | 12 | 48.6 |

TABLE 3-continued

Increased Cellulase Efficiency Through Use of Protein Treatment with Bovine Serum Albumin (BSA)

| FEED | Pretreatment Condition | Protein Prewash | Beginning Cellulose Content | Beginning Lignin content | Beginning Hemicellulose Content | Cellulase Applied (FPU/g cellulose) | Percent Conversion of Total Cellulose |
|---|---|---|---|---|---|---|---|
| Corn Stover | Flow through reactor 0.1% $H_2SO_4$ 180 C., flowrate of 20 ml/min, 20 min | None 1% Protein (BSA) | 68.6 | 17.1 | 11.2 | 20 15 | 81 80.4 |
| Corn Stover | Flowthrough | None 1% Protein (BSA) | 83.5 | 11.6 | 5.4 | 20 16 | 83.7 84.9 |
| Douglas Fir | Steam explosion (195 C., 4.5% $SO_2$ and 4.5 min) | None 1%Protein (BSA) | 56.3 | 46.1 | 8.2 | 20 15 | 64 66 |

Legend. 1% Protein = 1% Protein washing substrates (BSA)

As indicated in Table 3, protein treatment provided enhanced enzyme efficiency for all substrates tested. Specifically, protein pretreatment followed by hydrolysis using a lower cellulase concentration (mg/ml) was able to achieve the same conversion efficiency as did a higher cellulase concentration in cases where there was no protein pretreatment. Relatively greater amounts of enzyme were saved with increasing amounts of lignin content of the substrate. The results from this study demonstrate that the protein treatment improved the level of cellulase enzyme hydrolysis of cellulose even in the most recalcitrant of lignocellulosic biomass materials. It is shown here that protein treatment saves 10-25% FPU activity. For example, in the flowthrough reactor with 0.1% sulfuric acid, a 20 FPU/g cellulose of cellulase concentration produced a conversion efficiency of 81% without BSA prewash. This is compared to essentially the same conversion efficiency of 80.4% being provided by a cellulase concentration of 15 FPU/g cellulose as enabled by a 1% BSA prewash. Similarly, the cellulase hydrolysis yield per unit of cellulase is enhanced from 5% to 20%. In relation to the conversion of corn stover, about 50% conversion was achieved using 20 FPU/g cellulose of cellulase when the biomass was not treated with 1% protein wash, while only 12 FPU/g cellulose of cellulase produced essentially the same amount of conversion when the biomass was treated with a 1% protein (BSA) wash. This is about a 50% reduction in the amount of required enzyme. Thus, using the herein disclosed process of protein treatment, cellulase is decreased 5% to 50%, or 20% to 30%, or 20% to 40%, to provide essentially the same yield measured as percentage conversion of cellulose to carbohydrate.

EXAMPLE 2

Protein Treatment of High Lignin-containing Biomass

The present example demonstrates the utility of the inventive process for enhancing cellulose degradation and the efficiency of cellulase, or other cellulose-degrading enzymes, by inhibiting the protein binding capacity of lignin with protein/peptide having a non-specific lignin-binding affinity.

Two types of cellulose sources were studied. One type was α-cellulase—a purified cellulase without appreciable lignin. The other biomass type examined was corn stover (CS). Four samples were studied including α-cellulose without protein prewash, α-cellulose with protein prewash, CS with prewash and CS without prewash.

Each sample was washed at room temperature with 1%(w/w) BSA (aq) of an aqueous bovine serum albumin protein solution by filtering the protein solution through three passages while retaining solids on a medium glass filter at room temperature (the ratio of solid to protein solution is 1 g: 20 ml, the range of protein-absorbing capacities of lignin around 0.4 to 0.96 mg BSA/mg lignin). The solid residue was then further processed at a 2% solids concentration (g dry weight/100 mL) in 50 mM acetate buffer, pH 4.8 containing 40 mg/mL tetracycline and 30-mg/mL cycloheximide. Flasks were pre-incubated at 45° C. on the rotary shaker at 150 rpm for 10 min, and the enzymes were added to start the hydrolysis after acclimation. Aliquots of 0.5 mL were taken at different times (0, 0.2, 1, 4, 8, 12, 24, 48, 72 h), immediately chilled on ice and centrifuged at 5000 g for 10 min. Total sugar analyses were performed on the resultant supernatants.

The enzyme preparations used for all hydrolysis studies were obtained from Genencor. Treatments were performed with a complete cellulase supplemented with Novozyme™ 188 β-glucosidase, at a ratio of 1:1.75 (FPUase:CBUase). Enzymatic treatments were performed at 20 FPU/g cellulose. Total FPU were calculated by adding the activities of both the Celluclast™ and Novozyme™ 188. The cellulase preparation possessed 28 filter paper units (FPU)/mL, whereas Novozyme 188 possessed 8 FPU/mL, and 480 β-glucosidase IU/mL, and was supplemented to avoid end-product inhibition due to cellobiose accumulation.

Figure 2:
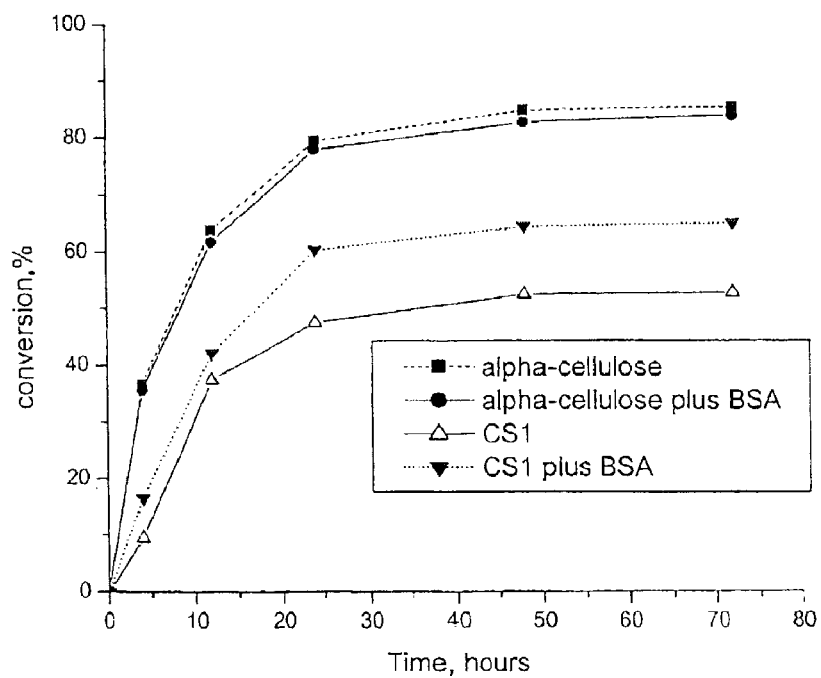
FIG. 2 shows solution concentration changes that result from hydrolysis of α-cellulose, in comparison with and without protein (BSA) addition.

FIG. 2 shows the results. The α-cellulose biomass sample showed a slight reduction in conversion efficiency resulting from BSA washing. While not intending to be limited to any particular mechanism of action or theory of operation of the invention, the reduction may be in the range of experimental error. Alternatively, the reduction may have resulted from the BSA having a slight affinity for cellulase, or to BSA interfering with the activity of cellulase, or perhaps both. As this difference is less than a 3% to 5% conversion efficiency, the BSA is deemed not to have appreciable affinity for cellulase. The corn stover samples, i.e., samples having a higher lignin content, show a conversion efficiency difference of about 15% after about 25 hours. While not intending to be limited to a particular theory, it may be that this difference exists because lignin is binding to BSA, and thereby increase the available cellulase.

EXAMPLE 3

Lignin-binding Protein/Peptide

The present example is provided to demonstrate the utility of using different lignin-blocking polypeptides and/or proteins in the conversion of lignocellulosic biomass.

The lignin-blocking protein demonstrated here to result in the reduction of cellulase enzyme required to convert biomass is BSA. BSA has a relatively high molecular weight of 66,000 Daltons. It is contemplated that other polypeptides and/or proteins that have the ability to block lignin binding will also be useful in the practice of the invention. Thus, while proteins and/or polypeptides having an average molecular weight from 2,000 Daltons to 300,000 Daltons is generally useful, proteins or polypeptides having the capacity to block lignin binding, and having a molecular weight in the range of about 55,000 Daltons to about 80,000 Daltons are expected to be particularly useful in the practice of the invention. Many proteins and polypeptides having a non-specific binding affinity for lignin may also be used to provide similar advantages. For example, proteins such as soybean protein (soybean flour, soybean meal) may be used to block lignin by preparing the polypeptide or protein composition in water, and using such a composition as a biomass prewash.

Lignin-blocking/binding polypeptides and proteins, as defined for purposes herein, are molecules that interfere with the ability of lignin to bind cellulase or other cellulose-hydrolyzing enzyme, and that has a high binding affinity for lignin and relatively insignificant binding activity (such as 1% to 3% w/w) for cellulose or for cellulose hydrolyzing enzyme, cellulase. These lignin-blocking/binding proteins and polypeptides may be further described as having a size of 55,000 Daltons to 80,000 Daltons. However, smaller or larger peptide fragments of BSA having a lower molecular weight but that retain sufficient lignin-binding activity may also be used in a prewashing treatment composition.

Lignin-blocking polypeptides and proteins that may be used in conjunction with the present invention are not contemplated to enhance efficiency of cellulose hydrolysis of biomass that does not comprise at least 5% lignin. This principle is demonstrated in FIG. 2. α-cellulose does not include an appreciable lignin component. Conversion of cellulose from α-cellulose pre-treated with 0.1% $H_2SO_4$, 180° C., 40 min. was examined. The percent conversion (%) and the rate of conversion (time, hours) of the α-cellulose biomass with protein-treatment and without protein treatment was relatively the same. α-cellulose+BSA reached 60% conversion at 12 hours, and 77% at 25 hours. α-cellulose without BSA reached 62-63% conversion at 12 hours, and 78% at 25 hours.

In contrast, a biomass having a higher content of lignin, such as corn stover (about 10 to 17% lignin), demonstrated a much more significant difference in the percent conversion. A much greater amount of cellulose in biomass was converted in the lignin-blocking polypeptide and/or protein-treated, lignin-containing biomass compared to the biomass not treated with a lignin-blocking polypeptide and/or protein. Using the same amount of cellulase enzyme (20 FPU/g cellulose enzyme loading), an observable increase in cellulose conversion after about 12 hours was demonstrated. This increase in cellulose conversion continued over time. CS+BSA reached 41% conversion at 12 hours, and 60% at 25 hours. CS without BSA reached 38% conversion at 12 hours and 46% at 25 hours. Here, a difference in cellulose conversion of the protein-treated corn-stover biomass of about 15% is demonstrated after 25 hours. This difference in the amount of cellulose conversion between the protein-treated and the non-protein treated biomass was maintained over the 70-hour period monitored.

EXAMPLE 4

Bioconversion of Steam-hydrolyzed Softwood with Protein Treatment

The present example demonstrates the further efficiency of bioconversion of a softwood lignocellulosic substrate that is pretreated with an acid catalyzed steam prehydrolysis step. The example provided here of a softwood lignocellulosic biomass was prepared from Douglas fir tree.

A fir tree sample was prepared as described in Boussaid et al, *Optimization of hemicellulose sugar recovery from a steam-exploded softwood (Douglas fir). Making a Business from Biomass in Energy, Environment, Chemicals, Fibers and Materials,* Proceedings of the Biomass Conference of the Americas, 3rd, Montreal, Aug. 24-29, 1997. The biomass was then processed through a pre-hydrolysis treatment of steam explosion. (195° C., 4.5% $SO_2$ for 4.5 minutes). The steam-explosion, prehydrolyzed biomass was then treated with a 10 FPU/g cellulose loading. The percent conversion by enzymatic hydrolysis was 64% after 72 hours. In contrast, when the steam exploded steam hydrolyzed biomass was treated with a 1% bovine serum albumin preparation, and then treated with a much lower amount of cellulase of 7.5 FPU/g cellulose, a conversion of 66% was obtained (See Table 1). The results demonstrate a reduction of 25% enzyme to produce slightly more conversion product from steam-exploded biomass of Douglass fir.

EXAMPLE 5

Enzyme Utilization/Preservation as Assessed by Filter Paper Activity (FPU) with and without Protein Treatment of Biomass The present example demonstrates that by pretreating a lignocellulosic biomass with lignin-blocking polypeptide and/or protein, the cellulase enzyme activity will be maintained in an active, unbound state. The relative activity of the enzyme (cellulase) is measured as filter paper activity (FPA activity %).

Figure 3:
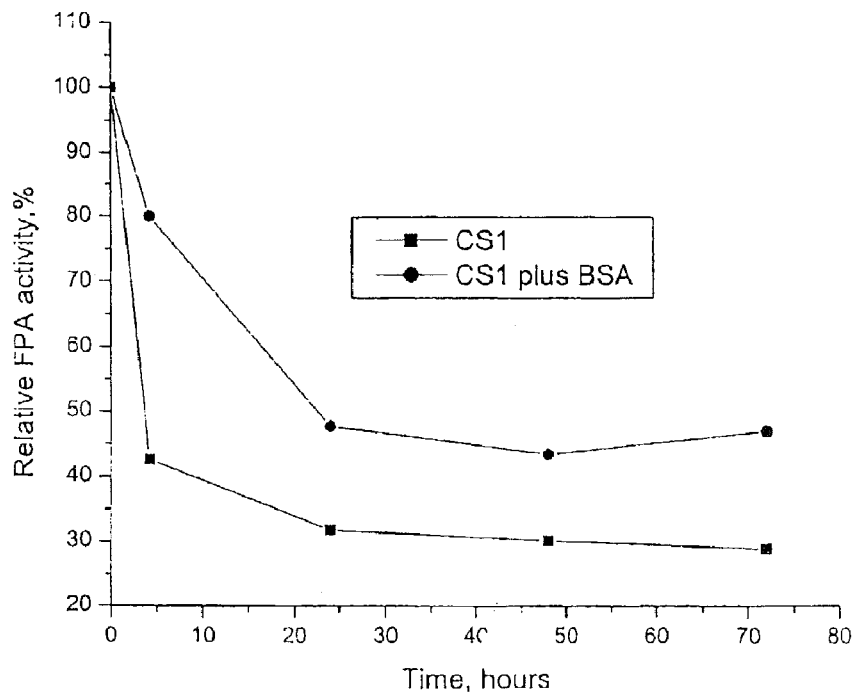
FIG. 3 shows filter paper activity (FPA) comprising changes during hydrolysis of corn stover with and without protein addition.

Corn stover (CS1), was pre-hydrolyzed with 0.76% $H_2SO_4$, at 160° C., for 10 minutes. Both the protein treated and the non-protein treated corn stover samples were examined starting with a 20 FPU/g cellulose enzyme loading. The amount of filter paper activity change was then monitored for the corn stover sample that had been treated with 1% BSA solution, as well as the corn stover sample that had not been treated with a 1% BSA solution. These results are shown as FIG. 3.

Relative FPA activity was preserved to a greater extent and for a longer period of time with biomass that had been treated with protein, compared to biomass that had not been treated with the protein. Relative FPA activity % fell from 100% to 42% after only about 4 hours, and then fell again to about 30% after 25 hours. In contrast, relative FPA activity fell only to about 80% after about 4 hours with the lignin-blocking protein treated biomass, and fell only to 50% relative FPA activity after 25 hours (See FIG. 3).

These data demonstrate that protein treatment effectively binds lignin in the corn stover biomass, and thereby precludes the lignin from binding available cellulase. For this reason, cellulase FPU activity was preserved for a longer period of time. This factor presents substantial economic advantages in using lignin-blocking protein pretreatment of lignin-containing biomass in bioconversion to ethanol.

EXAMPLE 6

Protein in Solution and Bioconversion Efficiency in Lignin vs Non-lignin Containing Biomass The present example is provided to demonstrate that a lignin-blocking polypeptide and/or protein, such as BSA, and the cellulase enzyme, are absorbed differently by a biomass that includes a lignin component, compared to a biomass that does not include a significant lignin component. This principal is demonstrated in the present example using α-cellulose, a biomass with little lignin, and CS, which does include at least 10% lignin.

Figure 4:
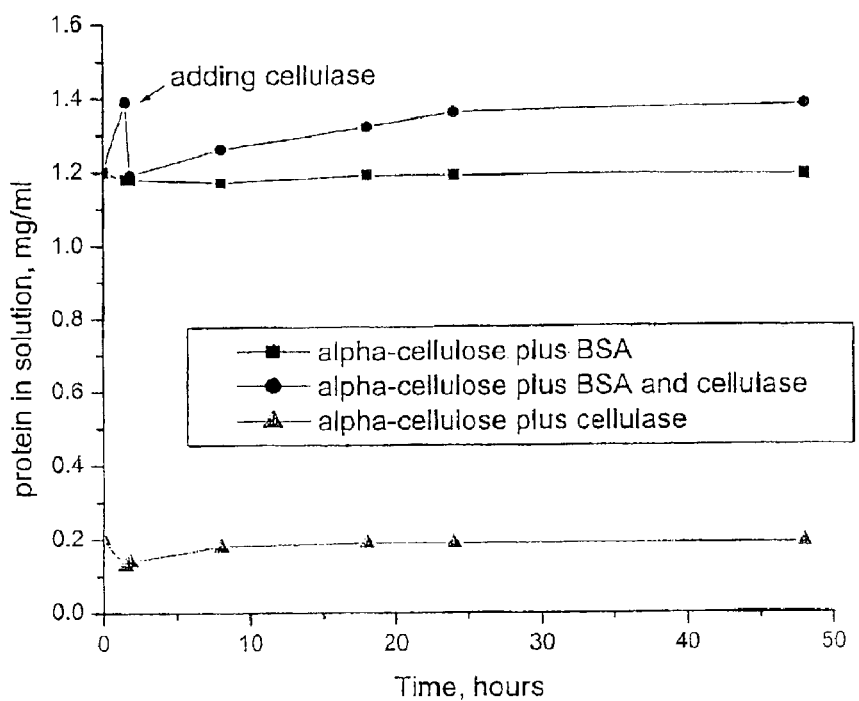
FIG. 4 shows total protein in supernatant during hydrolysis of α-cellulose with and without protein addition.

FIG. 4 demonstrates the analysis of total protein in solution over time during the hydrolysis of a biomass of α-cellulose (no lignin). The FIG. 4 study was conducted using an initial cellulase enzyme loading of 20 FPU/g cellulose enzyme. FIG. 4 shows that in the absence of lignin in the biomass (α cellulose), any protein that is added to the solution will not be adsorbed, and therefore remains a measurable component in the solution. At 0 hours, the α-cellulose plus BSA sample demonstrated a detectable amount of 1.2 protein in solution (mg/ml), which increased to 1.4 mg/ml upon the addition of cellulase at 10 hours (FIG. 4). The amount of protein in solution then dropped to 1.2 mg/ml at about 1 hour. About the same protein in solution value was obtained with a cellulose treated with BSA but to which cellulase had not been added. Over time, there was about a 0.1 to 0.15 mg/ml increase in the amount of measurable protein in solution in the α-cellulose sample to which both cellulase and a protein (BSA) treatment had been administered. No increase in the amount of measurable total protein in solution over time was demonstrated with the α-cellulose treated with BSA, but not cellulase.

FIG. 4 also shows that α cellulose to which cellulase have been added results in a relatively static protein in solution detectable level over the entire time period examined. As shown, about 0.2 mg/ml total protein in solution was evidenced with this sample at 0 hours, and this amount was relatively the same at 50 hours (See FIG. 4). In addition, FIG. 4. showed that protein had almost no effect on the rate of hydrolysis of α-cellulose. However, the rate of hydrolysis of CS1 was improved by pre-washed BSA treatment. These results suggest that protein has little effect on the catalytic mechanism of the cellulolytic enzymes. Therefore, it is likely that protein-blocking of the non-specific adsorption sites on lignin could be a key role of protein treatment in explaining the positive effect of protein on enzymatic hydrolysis of lignocellulose.

Figure 5:
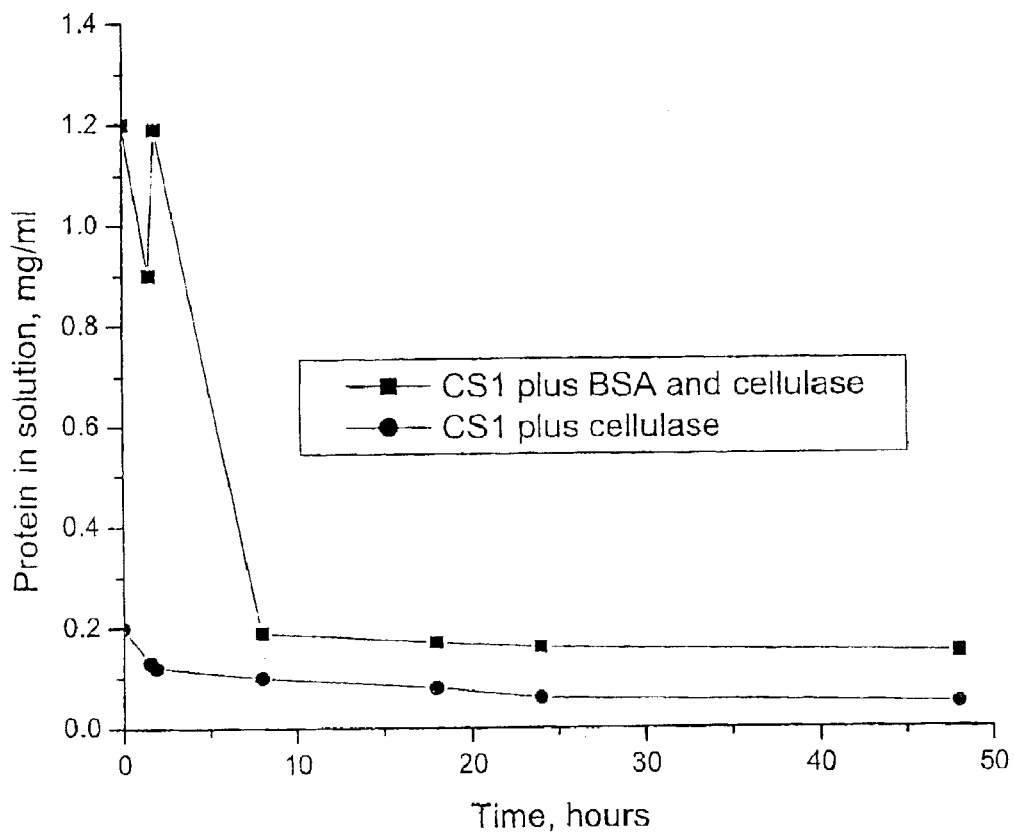
FIG. 5 shows protein in supernatant during hydrolysis of corn stover with and without protein addition.

FIG. 5 demonstrates the analysis of total protein in solution over time during hydrolysis of a biomass of corn stover (shown as CS1). The FIG. 5 study was conducted using an initial cellulase enzyme loading of 20 FPU/g cellulose enzyme. FIG. 5 demonstrates that in the presence of lignocellulosic biomass (CS), protein added in the form of the enzyme (cellulase) or protein wash (BSA), is adsorbed out of the solution. This reduction of total protein in solution is opined to reflect the adsorption of the BSA, the cellulase, or both, to the lignin component of the biomass. FIG. 5 demonstrates a significant loss of protein (including cellulose and/or BSA) in solution using a biomass that includes a lignin component. A protein-treated (BSA) biomass of corn stover demonstrated an initial protein in solution measure of 1.2 mg/ml. This measure dropped initially to 0.9 mg/ml at about 1 hour, and then rose again to 1.2 mg/ml upon the addition of cellulase at about 3 hours in the reaction. The protein in solution level fell dramatically at about 8 hours to about 0.2 mg/ml., and remained at this level over the entire period of the study, 50 hours.

Corn stover sample was also examined without having been treated with protein (BSA). Cellulase was added to this sample as well. The initial protein in solution value was much lower, at 0.2 mg/ml., at the 0 hour time point. This amount reduced to about 0.1 mg/ml after about an hour, and remained at this low level for the observed study period of study (50 hours).

Overall, the biomass sample with lignin demonstrated much lower levels of protein in solution over the entire test period compared to biomass that did not contain a lignin component. Thus, proteins, in the form of BSA, cellulase, or both, is absorbed by the lignin component of the biomass, and therefore protein is not detectable in solution. The proteins are absorbed to the lignin component of the biomass. This conclusion is supported by the observation of detectable protein in solution when examining biomass that does not include a lignin component. The protein in solution was highest in the α-cellulose biomass that had been treated with the BSA protein and cellulase. The α-cellulose plus BSA treatment demonstrated a lower total protein in solution than the sample to which cellulase and BSA was added. The α-cellulose biomass to which only cellulase had been added demonstrated a consistently lower amount of readable total protein of 0.2 mg/ml in solution over the entire test period. Here, the cellulase is acting to hydrolyze the available cellulose of the α-cellulose, unhindered by any lignin component.

The description of the specific embodiments reveal general concepts that others can modify and/or adapt for various applications or uses that do not depart from the general concepts. Therefore, such adaptations and modifications should and are intended to be comprehended within the meaning and range of equivalents of the disclosed embodiments. It is to be understood that the phraseology or terminology employed herein is for the purpose of description and not limitation.

What is claimed is:

1. A method for enhancing hydrolysis yield from a biomass having a high lignin content comprising the steps of:
    treating the biomass with a composition including means for blocking a lignin component of the biomass to provide a biomass having a treated lignin component,
    wherein the means for blocking the lignin component binds to a non-specific binding site on lignin and has a molecular weight between 55,000 and 80,000 Daltons and
    adding an effective amount of hydrolyzing enzyme to the biomass to hydrolyze a cellulose component of the biomass,
    wherein the means for blocking the lignin component is a protein selected from the group consisting of albumin, soybean protein, and combinations thereof.

2. The method of claim 1 further comprising the additional steps of:
    extracting the carbohydrate from cellulose;
    fermenting the carbohydrate in the presence of an ethanol converting microorganism for a period of time and under suitable conditions in a reaction mixture for producing ethanol; and
    extracting the ethanol from the reaction mixture.

3. A method for enhancing hydrolysis yield from a biomass having a high lignin content comprising the steps of:
    treating the biomass with a composition including a lignin-blocking polypeptide selected from the group consisting of albumin, soybean protein and combinations thereof to provide a biomass having a polypeptide-treated lignin component; and
    adding an effective amount of hydrolyzing enzyme to the biomass to hydrolyze the cellulose component of the biomass.

4. The method of claim 3, wherein the step of adding an effective amount includes use of hydrolyzing enzyme in an amount that is at least 20% less than would be required if the treating step were omitted.

5. The method of claim 3, wherein the biomass comprises at least 10% by weight lignin.

6. The method of claim 3, wherein the lignin-blocking polypeptide composition is further defined as comprising 0.1% to 10% by weight lignin-blocking polypeptide.

7. The method of claim 3, wherein hydrolysis yield from cellulose of biomass with a polypeptide treated lignin component is enhanced 5% to 20% compared to hydrolysis yield from cellulose of the biomass if the treating step were omitted.

8. The method of claim 3, wherein the biomass is further defined as comprising 10% to 50% by weight lignin.

9. The method of claim 3 further comprising the additional steps of:
    extracting the carbohydrate from cellulose;
    fermenting the carbohydrate in the presence of an ethanol converting microorganism for a period of time and under suitable conditions in a reaction mixture for producing ethanol; and
    extracting the ethanol from the reaction mixture.

10. A process for enhancing production of an organic compound from lignocellulosic biomass comprising:
    hydrolyzing the lignocellulosic biomass with steam, and acid or alkali to provide a treated biomass that comprises cellulose and lignin solids;
    washing the treated biomass solids with a lignin-blocking polypeptide selected from the group consisting of albumin, soybean protein and combinations thereof; and
    adding an effective amount of a cellulose-hydrolyzing enzyme to the treated biomass under conditions suitable for hydrolysis to produce carbohydrate,
    wherein said effective amount of hydrolyzing enzyme is at least 25% less than required to produce the carbohydrate if the washing step were omitted.

11. The process of claim 10 further comprising the additional steps of:
    fermenting the carbohydrate in the presence of an ethanol converting microorganism for a period of time and under suitable conditions in a reaction mixture for producing ethanol; and
    extracting the ethanol from the reaction mixture.

12. The process of claim 10 wherein the cellulose-hydrolyzing enzyme comprises cellulase.

13. The method of claim 3 wherein the cellulose-hydrolyzing enzyme comprises cellulase.

14. The method of claim 1, wherein the biomass comprises at least 10% by weight lignin.

15. The method of claim 1, wherein the step of adding an effective amount includes use of hydrolyzing enzyme in an amount that is at least 20% less than would be required if the treating step were omitted.

16. The method of claim 1 wherein the biomass comprises wood, agricultural or forestry residuals, grasses or a combination thereof.

17. The method of claim 1 wherein the composition is further defined as comprising 0.1% to 10% by weight of the means for blocking the lignin component.

18. The method of claim 1 wherein hydrolysis yield from cellulose of biomass with the treated lignin component is enhanced 5% to 20% compared to hydrolysis yield from cellulose of the biomass if the treating step were omitted.

19. The method of claim 1 wherein the cellulose-hydrolyzing enzyme comprises cellulase.

20. The method of claim 1 wherein the biomass is further defined as comprising 10% to 50% by weight lignin.

* * * * *